(12) United States Patent
Birk et al.

(10) Patent No.: US 7,727,143 B2
(45) Date of Patent: Jun. 1, 2010

(54) LOCATOR SYSTEM FOR IMPLANTED ACCESS PORT WITH RFID TAG

(75) Inventors: Janel Birk, Oxnard, CA (US); Donald Weihrich, Liverpool, NY (US)

(73) Assignee: Allergan, Inc., Irvine, CA (US)

( * ) Notice: Subject to any disclaimer, the term of this patent is extended or adjusted under 35 U.S.C. 154(b) by 883 days.

(21) Appl. No.: 11/444,702

(22) Filed: May 31, 2006

(65) Prior Publication Data
US 2007/0282196 A1 Dec. 6, 2007

(51) Int. Cl.
*A61F 2/00* (2006.01)
(52) U.S. Cl. ........................................................ 600/37
(58) Field of Classification Search ............. 600/29–32, 600/37; 128/DIG. 25, 897–899; 606/151–158
See application file for complete search history.

(56) References Cited

U.S. PATENT DOCUMENTS

| | | | |
|---|---|---|---|
| 5,171,228 A * | 12/1992 | McDonald | 604/175 |
| 5,300,120 A | 4/1994 | Knapp et al. | |
| 5,674,288 A | 10/1997 | Knapp et al. | |
| 5,725,578 A | 3/1998 | Knapp et al. | |
| 5,833,603 A | 11/1998 | Kovacs et al. | |
| 5,855,609 A | 1/1999 | Knapp | |
| 5,923,001 A * | 7/1999 | Morris et al. | 177/245 |
| 5,977,431 A | 11/1999 | Knapp et al. | |
| 6,305,381 B1 * | 10/2001 | Weijand et al. | 128/899 |
| 6,511,490 B2 * | 1/2003 | Robert | 606/151 |
| 6,622,043 B1 | 9/2003 | Kraus et al. | |
| 6,635,014 B2 | 10/2003 | Starkweather et al. | |
| 6,636,769 B2 | 10/2003 | Govari et al. | |
| 6,638,231 B2 | 10/2003 | Govari et al. | |
| 6,647,298 B2 | 11/2003 | Abrahamson et al. | |
| 6,647,299 B2 | 11/2003 | Bourget | |
| 6,648,823 B2 | 11/2003 | Thompson | |
| 6,658,300 B2 | 12/2003 | Govari et al. | |
| 6,664,897 B2 | 12/2003 | Pape et al. | |
| 6,665,558 B2 | 12/2003 | Kalgren et al. | |
| 6,666,821 B2 | 12/2003 | Keimel | |
| 6,667,725 B1 | 12/2003 | Simons et al. | |
| 6,671,550 B2 | 12/2003 | Iaizzo et al. | |
| 6,675,049 B2 | 1/2004 | Thompson et al. | |
| 6,704,602 B2 | 3/2004 | Berg et al. | |

(Continued)

FOREIGN PATENT DOCUMENTS

WO   WO2004/030536   *   4/2004

*Primary Examiner*—John P Lacyk
(74) *Attorney, Agent, or Firm*—Linda Allyson Fox; Allergan, Inc.

(57) ABSTRACT

An access port locator system for adjustable gastric bands. The system includes an access port with an RFID tag with its antenna adjacent to the receiving portion of the port. The system includes a locator with radio frequency transmitter/receiver circuitry for sending read or interrogation signals to the RFID tag and for sending write signals to the tag to write treatment data to memory of the RFID tag. The locator also includes an antenna array with four patch antenna arranged in pairs to model two monopulse radar antenna systems. The locator also includes processor(s) and logic modules/circuitry for processing the tag response signals received by the antenna array to determine location information for the RFID tag and associated port, i.e., to identify the center of the port relative to the antennae array or array face such as with strength and direction information relative to the array face.

22 Claims, 8 Drawing Sheets

U.S. PATENT DOCUMENTS

| | | | |
|---|---|---|---|
| 7,191,011 B2 * | 3/2007 | Cantlon | 607/60 |
| 2002/0032435 A1 * | 3/2002 | Levin | 606/1 |
| 2004/0250819 A1 * | 12/2004 | Blair et al. | 128/899 |

* cited by examiner

LOCATOR SYSTEM FOR IMPLANTED ACCESS PORT WITH RFID TAG

BACKGROUND OF THE INVENTION

1. Field of the Invention

The present invention relates, in general, to devices and methods for controlling obesity, and, more particularly, a system and method for accurately locating a port of an inflation/deflation tube for an implanted gastric band to allow a needle to be inserted into the center of the port. The present invention also relates to the use of radio frequency identification (RFID) technology for reading and writing data to an implanted medical device (IMD) such as a gastric band inflation/deflation port.

2. Relevant Background

Severe obesity is an increasingly prevalent chronic condition that is difficult for physicians to treat in their patients through diet and exercise alone. Generally, gastrointestinal surgery promotes weight loss by restricting food intake, and more specifically, restrictive operations limit food intake by creating a narrow passage or "stoma" from the upper part of the stomach into the larger lower part, which reduces the amount of food the stomach can hold and slows the passage of food through the stomach. Initially, the stoma was of a fixed size, but physicians have more recently determined that the procedure is more effective if the stoma can be adjusted to alter its size. One of the more commonly used of these purely restrictive operations for obesity is adjustable gastric banding (AGB).

In an exemplary AGB procedure, a hollow band (i.e., a gastric band) made of silicone elastomer is placed around the stomach near its upper end, creating a small pouch and a narrow passage (i.e., a stoma) into the rest of the stomach. The band is then inflated with a saline solution by using a non-coring needle and syringe to access a small port that is placed under the skin. To control the size of the stoma, the gastric band can be tightened or loosened over time by the physician or another technician extracorporeally by increasing or decreasing the amount of saline solution in the band via the access port to change the size of the passage or stoma.

After a port has been placed in a patient, it is often difficult to locate the port, and to support insertion of a needle, the center of the port needs to be located for the technician or physician who is injecting or withdrawing saline. The location process is complicated as the port is typically positioned beneath the patient's skin and sometimes beneath other tissue such as fat. Presently, port location is accomplished through the use x-rays and or fluoroscopes. However, these technologies are expensive to use, require an additional technician to operate the location equipment, and may require the port to be manufactured with materials that are more suited for locating but that are less biocompatible. As a result, the medical industry continues to demand a less complex and costly devices and methods for locating the inflation/deflation port for adjustable gastric band systems while requiring that the port locating devices be accurate and relatively easy to use.

Additionally, with implantable medical devices (IMDs), it is often desirable to be able to read data from the IMD and, in some cases, to write data to the IMD. For example, medical device developers have created IMDs that include passively powered radio frequency (RF) transponders and these transponders are powered to communicate with an external transmitter/receiver. The passive RF device has programmable memory for storing information related to the device and/or the patient. For example, the information may include patient demographics, implant data, and manufacturer or device information (e.g., manufacturer ID, IMD model, serial numbers, and the like). In other cases, sensors are provided with the IMD to obtain patient information such as blood pressure, and the sensor collected data is transmitted from the IMD to an external transmitter/receiver device.

Some of these RF-based devices require the transmitter/receiver to be held within a relatively close distance of the implanted device to obtain accurate signals from the IMD, and efforts have been made by developers to measure the quality of the RF signals received from the transponder on the IMD to determine when the transmitter/receiver is within an acceptable range of the IMD transponder and an audio signal may be used to indicate an acceptable relative distance between the two devices. However, the determination that an IMD and a transmitter/receiver are within a particular distance from each other is not particularly useful for inserting a needle into a center of a gastric band port where the accuracy required is measured in millimeters.

Hence, there remains a need for an improved method and system for locating a center of an inflation/deflation or "access" port of a gastric band after it has been implanted within a patient or for locating other implanted IMD accurately. Preferably, such a method and system would provide effective feedback to a technician or physician attempting to insert a needle within the center of the access port so as to facilitate accurate insertion of the needle. Further, it is preferable that such a method and system be compatible with reading data from the access port (or other IMD) and, in some cases, for writing data to the access port (or other IMD).

SUMMARY OF THE INVENTION

The present invention addresses the above and other problems by providing a port locator system and method for use in gastric band systems for accurately locating the access port for an inflate/deflate line to allow an operator to adjust the size of a stoma on a periodic basis. The port locator system includes an RFID-enabled access port, i.e., an access port with an RFID tag mounted on it with the antenna of the tag being positioned such that response signals indicate the center of the port (or a face used to receive needles), which can be achieved by coiling the antenna along the wall of the port (or about the periphery of the receiving surface). The port locator system also includes a locator with RF transmitter/receiver circuitry for sending read or interrogation signals to the RFID tag and for sending, in some embodiments, write signals to the tag to write patient treatment data (such as patient information and adjustment information for the band) to memory of the RFID tag. The locator also includes an antenna array that in some cases includes four patch antenna arranged in pairs to model two monopulse radar antenna systems. The locator also includes processor(s) and logic modules/circuitry for processing the tag response signals received by the antenna array to determine location information for the RFID tag and associated port, i.e., to identify the center of the port relative to the antennae array (or array face) such as with strength and direction information relative to the array face.

More particularly, a gastric band system is provided that is adapted for locating an access port with radio frequency technology. The system includes a gastric band with a fill line having an access port for receiving a needle and that has an RFID tag. A locator is provided in the system for locating the access port. The locator includes a radio frequency transmitter that generates a read or interrogation signal, which the RFID tag on the port responds to by generating a tag response signal. The locator also includes an antenna array that is used by the RF transmitter to transmit the interrogation signal and is also functions to receive the tag response signal from the RFID tag. The locator uses a location processing module to process the tag response signal to determine location information for the access port, which may include strength information and direction information relative to an antenna array face and which may be displayed via a GUI or other user interface on a display element of the locator.

The access port may include a surface for receiving the needle and the RFID tag typically includes an antenna (such as a coil antenna) that is positioned about the periphery of the receiving surface of the port (such as on a port wall defining the receiving surface) such that the location information determined for the access port is indicative of the center of the receiving surface. The antenna array may be made up of two pairs of antennae that are positioned an equal distance from each other (within the pair and from adjacent ones of the antennae) and an predetermined distance from a central axis of the antenna array (i.e., a line passing through a point in the plane containing the antenna pairs that is substantially in the center of the antennae). The location processing module preferably functions to process difference signals for each of these pairs of antennae to determine the location information for the access port, with the difference signals being generated in the antenna array based upon the tag response signal as received by each of the antennae. The locator may include a receiver processing module that operates prior to the location processing module to generate an in-phase tag response signal and a quadrature tag response signal from each of the difference signals. The locator may also include a tag data processing module that processes a sum signal generated by the antenna array based on the tag response signal to obtain tag data stored in memory of the RFID tag, whereby the locator is able to read data on the RFID tag. Further, the RF transmitter of the locator may be operated to generate a write signal, e.g., based on operator input entered via a keypad or other I/O component of the locator, that is transmitted to the RFID tag via the antenna array, with the RFID tag operating in response to store data in the write signal to persistent tag memory, whereby the locator is operable to write patient treatment data to the access port.

DETAILED DESCRIPTION OF THE PREFERRED EMBODIMENTS

In brief, the invention is directed to a gastric band system with an access port locating functionality that enables an operator (e.g., a physician or technician) to accurately locate an access port of a fill tube (or inflation/deflation line) for a gastric band after implantation in a patient. The invention may also be said to be directed to a port locator method and system for use with adjustable gastric bands. The port locator method is useful for locating an access or inflation port to a degree of accuracy which allows a doctor or technician to insert a needle into the center of the access port. To this end, the access port of the gastric band system is RFID-enabled and a locator is operated to communicate with the RFID-enabled or tagged port, which may include read-only or read/write memory for storing information related to the port/band and/or the patient. The term "locator" is used herein to describe technology and components that may include or build upon standard RFID "readers" or "interrogators" (e.g., the locator may be considered an enhanced/modified RFID reader or interrogator).

The locator may be a handheld device that includes a microprocessor, memory, a specially configured antenna array or system, and logic/circuitry that function in conjunction to determine precisely the location of the port based on RF signals transmitted from the port and to display the location information to an operator via a display and a graphical user interface. The handheld locator typically is also adapted with a receptacle for holding a syringe and needle so facilitate insertion of the needle in the center of the port base on displayed location information. Further, the locator is operable to read data from the port's RFID tag memory that is displayed to the operator on the display and, optionally, is operable to write data to the port's RFID tag memory for long term storage that can later be read by the locator or other RFID devices. For example, this data or information may include band or port serial number, size and/or type of band, patient information and/or demographics, adjustment volumes, and adjustment dates/times, which allows the device, patient, and adjustment or treatment history to be stored on or at the access port of the gastric band. The access port location features of the invention can be used with numerous gastric band designs and are particularly useful for those that include an inflatable portion, e.g., an inner lumen, that is expanded or contracted by increasing or decreasing the volume of fluid contained therein via an access port (or inflation/deflation port).

Figure 1:
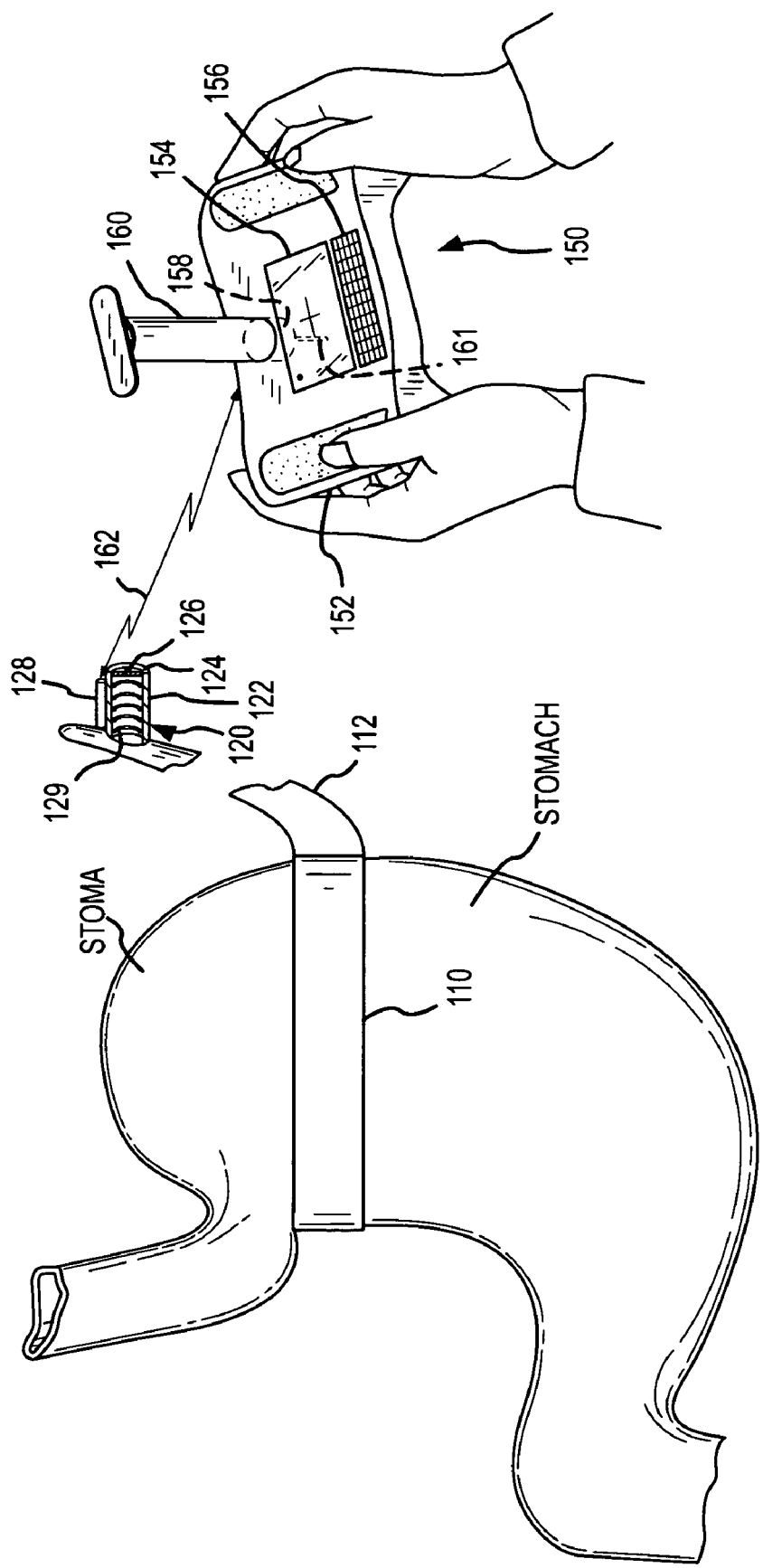
FIG. 1 illustrates an adjustable gastric band system with an RFID port locator system according to the present invention as it may be used in treating a patient.

FIG. 1 illustrates a gastric band system or apparatus 100 as it may appear when installed in a patient being treated for morbid obesity. As shown, the system 100 is being used to form a stoma or smaller opening in the upper portion of the stomach near the esophagus to restrict food intake and flow. It is often useful or even necessary to vary the size of the stoma to properly treat a patient, e.g., to initially set a size of the stoma and then, later alter its size by adding or withdrawing fluid via port 120. Hence, the gastric band system 100 is adapted for adjustment of its size. The gastric band system 100 includes a gastric band 110 that is inflatable by external or extracorporeal actions via a fill tube or line 112 that is connected to an access port 120 through which fluid can be pumped into the inflatable portion or member of the gastric band 110. Such a filling if typically performed as part of an initial sizing of the stoma as part of the implanting process performed by the physician or other technician and at later treatment sessions. To perform such filling (and withdrawing) of the band 110, the physician or technician needs to be able to accurately locate the access port 120 even though it may be beneath skin and other tissue.

The band 110 and other components of the system 100 are implanted in the same or similar surgical procedure as used with existing expandable or inflatable gastric bands. For example, a surgeon would typically dissect the tissues around the stomach to create a tunnel for the band 110. The band 110 is then introduced into the patient's abdomen, e.g., through an 18 mm or other sized trocar or the like or directly through the trocar hole in the skin. The band 110 is then tunneled in place and positioned around the stomach. The other components of the system 100 are placed near the stomach (such as just below the skin on top of the sternum or on the rectus muscle sheath proximate the access port) with fluid connection provided via port 120 and fill/drain line 112 to the gastric band 110 and particularly to the inflatable or expandable member or portion of the band 110.

The access port 120 of the gastric band system 100 includes a wall 122 extending away from the tube 112 to a face or surface 124 that has a sealable or self-sealing opening with a center 126, e.g., the port 120 is formed to receive a needle (such as needle 161) but to seal when the needle is withdrawn to block flow of fluid out of the tube 112. To inflate or deflate the band 110 to adjust the stoma, an operator of the system 100 locates the port 120 with such accuracy that the face or surface 124 and the port center 126 can be identified and a needle (such as needle 161) guided into the port 120 at the center 126.

To this end, the port 120 is "RFID-enabled" by the inclusion of an RFID tag 128 that is mounted on the wall 122 of the port 120. The antenna 129 of the tag 128 preferably is positioned to extend about the periphery or circumference of the generally circular face or surface 122 such as by being mounted on the port wall 122. In this manner, the signals 162 transmitted from the RFID tag 128 in response to interrogation signals from a locator 150 facilitate location or identification of the center 126 of the surface or face 124 of the port 120. Alternatively, the antenna 129 may be mounted within the tag 128 and the antenna's location or offset relative to the center 126 may be measured/predetermined and utilized in the location processing modules or logic of the locator 150 to determine the location of the center 126 based on the signals 162.

The system 100 further includes a locator 150 that includes a display element 154 that is used to display data read from the port tag 128 via wireless or RF communications 162 with the RFID tag 128 and antenna 129, to display data such as adjustment or patient information to be written to memory of the RFID tag 128, and, significantly, to display location information or information useful for positioning the handheld locator 150 relative to the center 126 of port 120. The locator device 150 also includes a keypad or other input area 156 for allowing an operator to enter data or input to be written to the RFID tag 128 or to query for read data or the location of port 120. The locating method performed by the locator 150 is discussed in detail below with reference to FIGS. 2-8.

The locator 150 as shown may include a recessed surface or receptacle 158 in its housing 152 for receiving a syringe 160 with a needle 161. This may be useful for facilitating positioning of the needle 161 on the center 126 of the port face 124 while viewing the location information on the display 154. The receptacle 158 preferably would include a channel or hole that allows the needle 161 to extend through the locator 150 for insertion into the port 120 when the locator housing 152 is properly positioned relative to the port 120 as indicated on the display 154. In some embodiments, the receptacle 158 is positioned in the housing 152 such that the needle 161 of the syringe 160 extends transverse (and often perpendicularly) to a board or mounting plate (e.g., a planar element) on which the antenna system is mounted, and more specifically, so as to extend through the center of antennae in such an antenna system (as is explained in more detail below). Such a positioning allows ready translation of the determined location of the port 120 to the relative position of the handheld locator 150. Of course, the syringe 160 may be mounted on the housing 152 in a different manner (or even provided separately) with the relative position of the needle 161 of the syringe to the antenna system being taken into account to assist an operator in inserting the needle 161 into the center 126 of the port face 124.

The gastric band 110 may take many forms to practice the invention. For example, but not as a limitation, the gastric band 110 may be configured similar to the gastric bands described in U.S. Pat. Nos. 5,226,429 and 5,601,604, which are incorporated herein in their entirety by reference. Alternatively, the gastric band 110 may include one of the gastric bands available from Inamed Corporation (e.g., one of the bands in the LAP-BAND™ family of expandable gastric bands such as the 9.75, 10.0, 11.0 cm, the VG, or AP LAP-BANDs). Other gastric bands from various band manufacturers/distributors that could be used for this application include, but are not limited to: the Obtech (Ethicon) band, the AMI band, the Heliogast band, the Minimizer (Pier) band, and Cousin Bioband.

Figure 2:
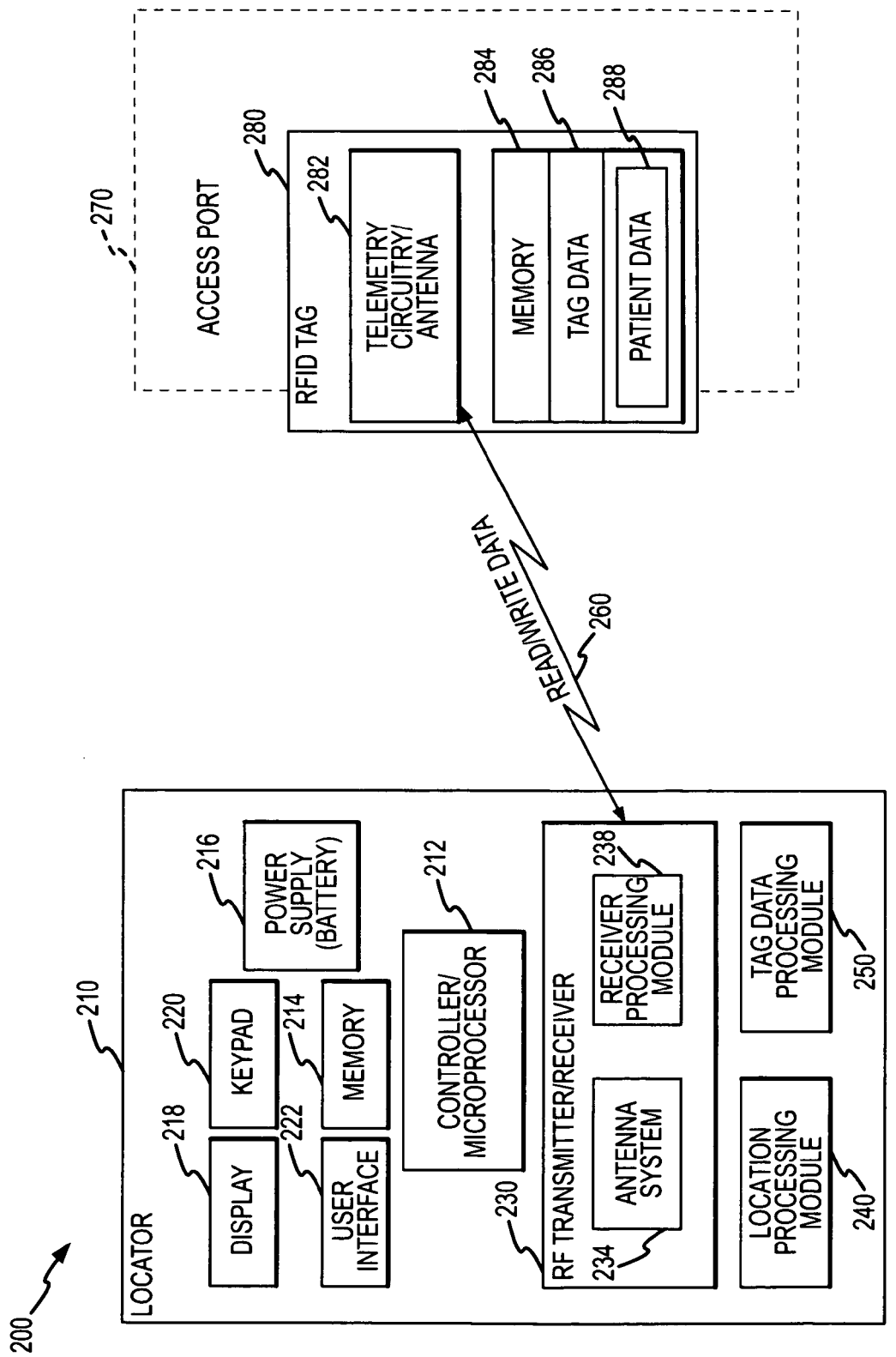
FIG. 2 is a block diagram of a port locator system of the invention, such as may be used in the gastric band system of FIG. 1 to locate the an implanted access port.

FIG. 2 illustrates in block form a port locator system 200 such as may be used within a gastric band system (e.g., system 100 of FIG. 1). As shown, the port locator system 200 includes a locator 210 that communicates read/write data via RF or wireless signals 260 with an RFID tag 280 that is mounted on or provided as an integral part of an access port 270 for a gastric band (not shown). The locator 210 is typically a handheld device and includes a controller/microprocessor 212 that manages operation of components and logic on the locator 210. The functionality of the locator 210 as described herein (and with reference to FIGS. 3-8) may be implemented with software or logic and/or with appropriate hardware/circuitry components. The locator 210 includes memory (RAM and/or ROM), a power supply 216 such as a rechargeable battery or the like, a display 218 such as an liquid crystal display (LCD) or the like, a keypad and/or other input device 220, and a user interface 222 (such as a GUI for use in displaying location of the port 270 relative to the locator 210 on the display 218).

The locator 210 functions to communicate with the RFID tag 280 and in this regard, the locator 210 includes an RF transmitter/receiver 230 with an antenna system 234 and a receiver processing module 238 (each of which is described further below). The locator 210 further includes a location processing module 240 for determining the location of the port 270 relative to the locator 210 and more specifically, relative to the antenna system 234. A tag data processing module 250 is provided for processing data read from the tag 280 and for use in displaying the data on display 218 via user interface 222 and for facilitating write operations to the tag 280.

The RFID tag 280 is provided on the port 270 so as to RFID enable the port and allow it to be located by the locator 210. The RFID tag 280 includes at least telemetry circuitry/antenna 282 and memory 284 for storing tag data 286, such as serial number, band type and size, and the like, and patient data 288, such as adjustment or treatment information and demographic information. The RFID tag 280 may take various forms to practice the invention. Typically, in a read/location operation of the system 200, the RF transmitter/receiver 230 (or "reader") initiates collection of data 286, 288 by sending a message 260 to the tag 280. The RFID tag 280 is typically an inductively coupled RFID tag with the circuitry 282 being powered by the magnetic field generated 260 by the RF transmitter/receiver 230 as the antenna picks up the magnetic energy and, then, the tag 280 communicates via signals 260 with the receiver 230 of locator 210 via antenna system 234. The telemetry circuitry/antenna 282 may include a silicon microprocessor or chip and a metal coil or other type of antenna (such as conductive carbon ink or the like). In other embodiments, the RFID tag 280 is an active tag powered by a battery (not shown) or is a passive tag that is capacitively coupled for powering by the locator 210 (rather than being passive and powered inductively by the locator 210).

During operation, the tag 280 responds to the locator 210 via signals 260 when it is within the locator's field, i.e., the tag 280 has a range that is typically selected to be relatively short such as less than about 20 feet and more typically very short such as less than about 2 feet or the like. The frequency range may also vary significantly to practice the invention and in some short range applications, the frequency utilized may be a low frequency such as one selected in the range of 30 KHz to 600 KHz or higher. The RFID tag 280 is preferably selected to have relatively good propagation, i.e., a good ability to perform tag-locator communication through objects and material such as human tissue. The antenna 282 in the tag 280 may be selected to have directional coverage (rather than being omni-directional) to provide RF coverage that is stronger in a specific direction such as in the direction perpendicular to the face of the port to facilitate identification of the center of the port 270. The memory 284 may be read only, read/write, or even write once/read many and may vary in size such as 16 bits to 512 kBytes or larger.

According to the invention, port location is accomplished by processing signals from an RFID tag provided with an access port of a gastric band. To this end, antenna systems of the invention (such as those in locator 150 of FIG. 1 and antenna system 234 of FIG. 2) are modeled after a monopulse radar antenna system 300 shown conceptually in FIG. 3. In the antenna system 300, a pair of antennae such as patch antenna operates to form a sum beam pattern 330 that maximizes directly over the antenna system face. Also, the monopulse radar antenna system 300 operates to form a delta beam pattern that appears as two adjacent lobes 310, 320 and that has a null response directly over the antenna system face. The behavior of the modeled system 300 can be used and expanded upon to enable detection of the location of a transmitting device, such as an RFID tag or its antenna provided on an access port.

The locator system of the invention can be thought of as containing three component parts: an antenna system with RF beam forming components (e.g., antenna system 234 of FIG. 2), an analog receiver processing module (e.g., element 238 of FIG. 2), and a digital signal detection/control interface component (e.g., elements 240 and 250 of FIG. 2). Each of these components is described in the following discussion with reference to FIGS. 4-8.

Figure 3:
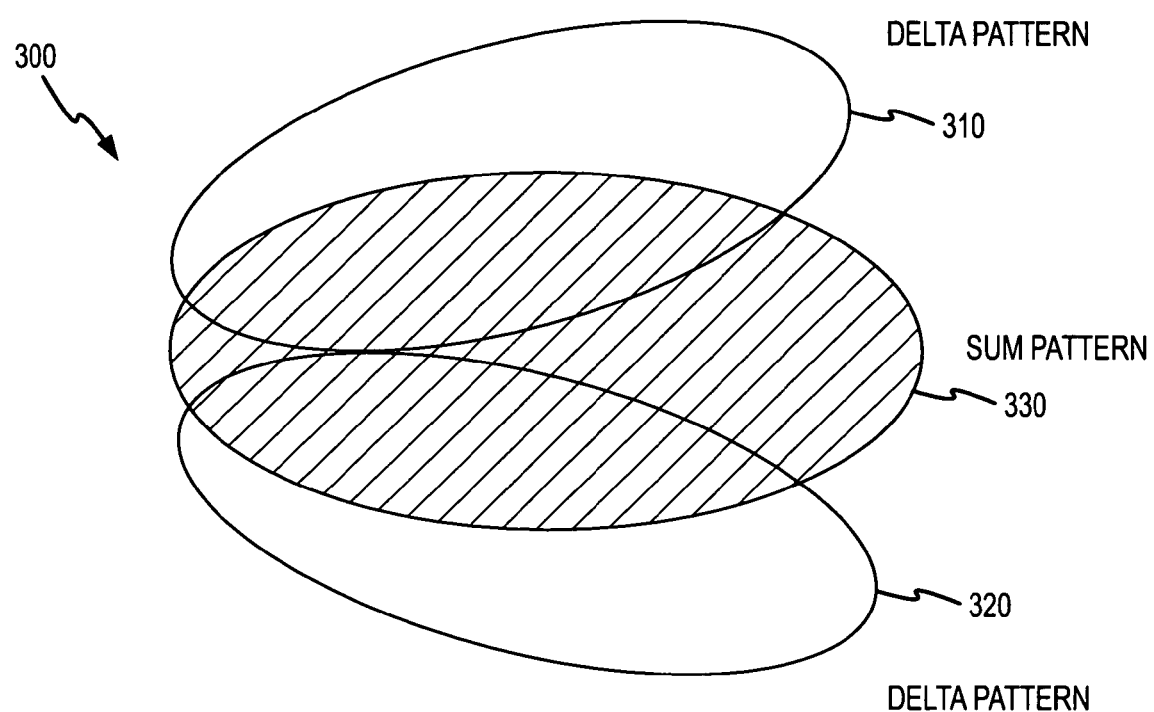
FIG. 3 illustrates generally the monopulse antenna concept that is incorporated in the use of paired antennae in the antenna system of embodiments of the invention.
Figure 4:
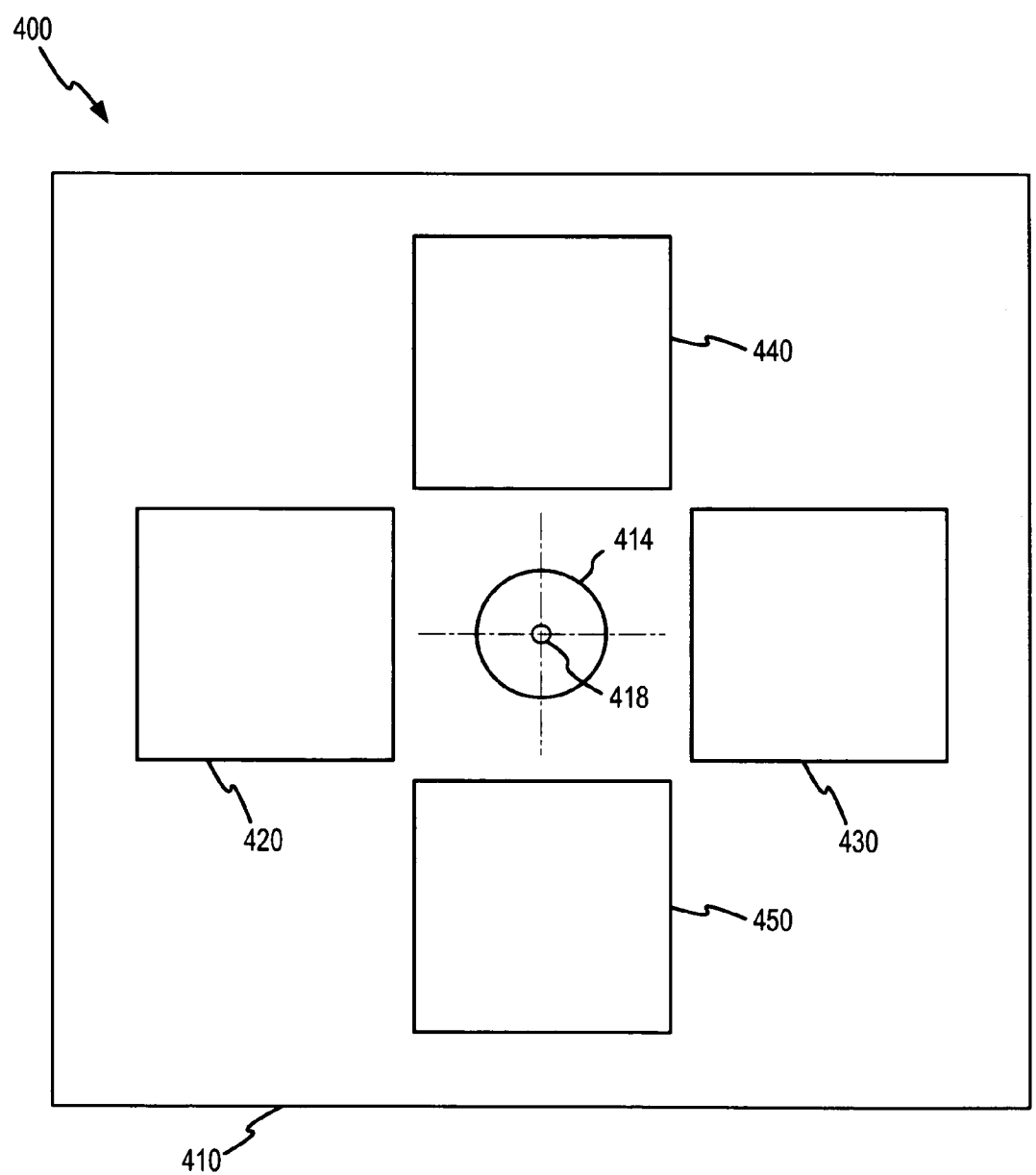
FIG. 4 is a view of the antenna system of one embodiment of the invention with a portion of the locator housing removed to show two pairs of patch antennae with a recessed surface for receiving a syringe/needle centered between the antennae.

FIG. 4 illustrates one useful embodiment of an antenna system 400 for use in locators of the present invention. As shown, the antenna system 400 is provided as a two-dimensional (2-D) array of paired antennae 420 and 430 and paired antennae 440 and 450. The antennae 420-450 may be patch antenna or some other useful form of antenna for communicating with an RFID tag, and the paired antennae 420-450 are mounted on a planar base, board, or plate 410. More specifically, the antennae 420-450 are arranged to form two monopulse radar antenna systems such as shown in FIG. 3. The two pairs of antennae 420, 430 and 440, 450 are arranged to form a diamond shape with an up/down set 440, 450 and a left/right set 420, 430. The antennae 420-450 are spaced equidistantly from each other and about a center that is marked with dashed lines in FIG. 4. In embodiments in which the syringe is received and directed through the locator housing, the antennae mounting element or plate 410 includes a recessed surface 424 in the center of the antenna system formed by antennae 420-450 and a hole or channel 418 that extends through the plate 410 is provide to allow a needle to pass through the plate 410.

Figure 5:
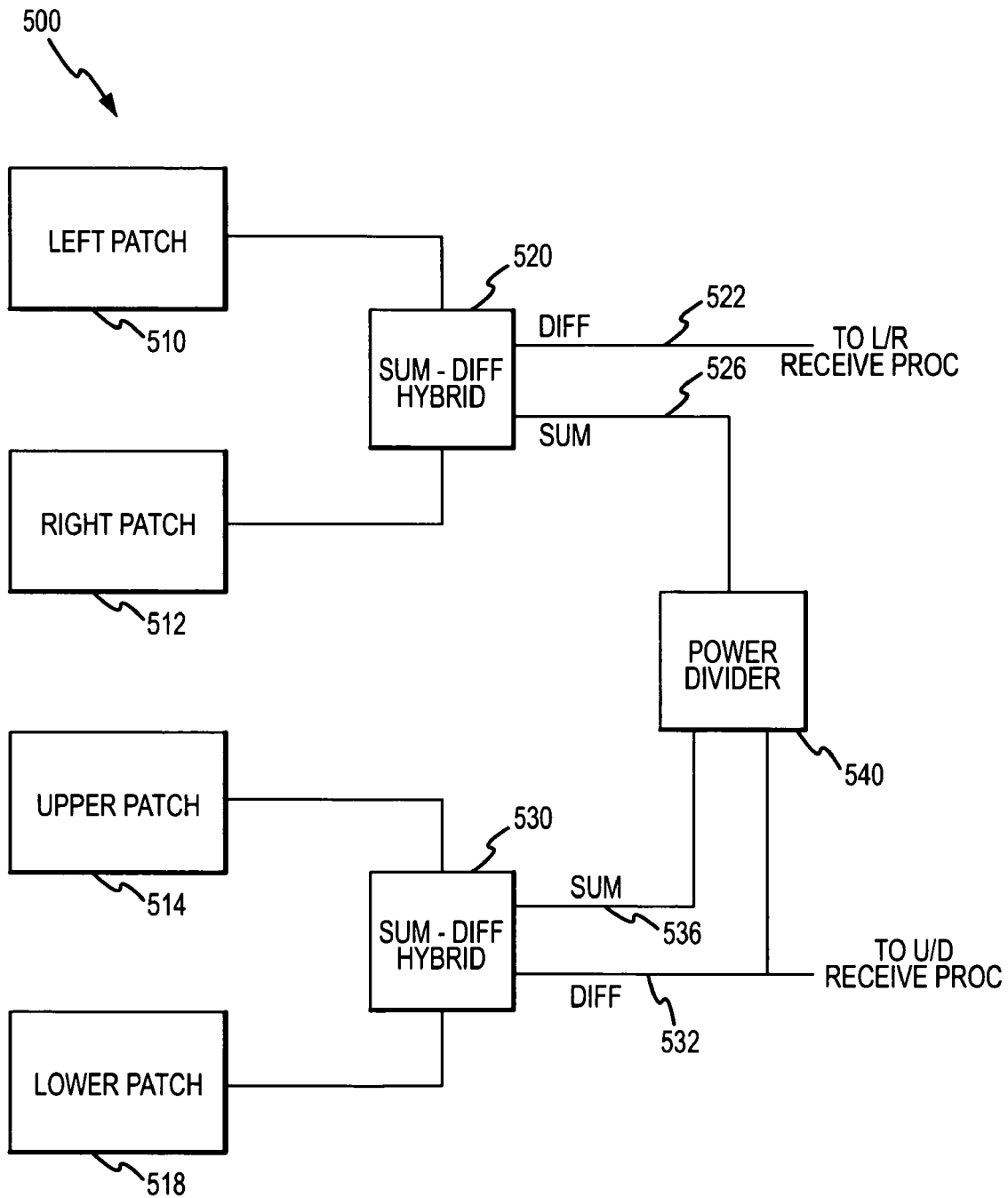
FIG. 5 is a functional block diagram of an embodiment of the antenna system provided in a locator of the present invention.

FIG. 5 illustrates an antenna system 500 in block form to better illustrate circuitry useful in implanting a locator device to locate access ports. As shown, the system 500 includes a left patch 510 that is paired with a right patch 512 and an upper patch 514 that is paired with a lower patch 518 (and that may be arranged physically as shown in FIG. 4). One pair, formed by two of the opposing antennae such as the left and right patch antennae 510, 512, is fed with a signal divider circuit 520 that provides the sum 526 of the two antenna signals to a power divider 540 as well as outputting the difference 522 to the receiver processing module. Similarly, the other pair, formed by the other orthogonal pair such as the upper and lower patch antennae 514, 518, is fed with a signal divider circuit 530 that provides the sum 536 to the power divider 540 as well as outputting the difference to the receiver processing module. Both feeds are bi-direction, e.g., the feeds to the antennae perform the same signal manipulation for signals radiating from the antenna elements 510-518 as for signals being received by the antenna elements 510-518 (i.e., emanating from the RFID tag).

Figure 6:
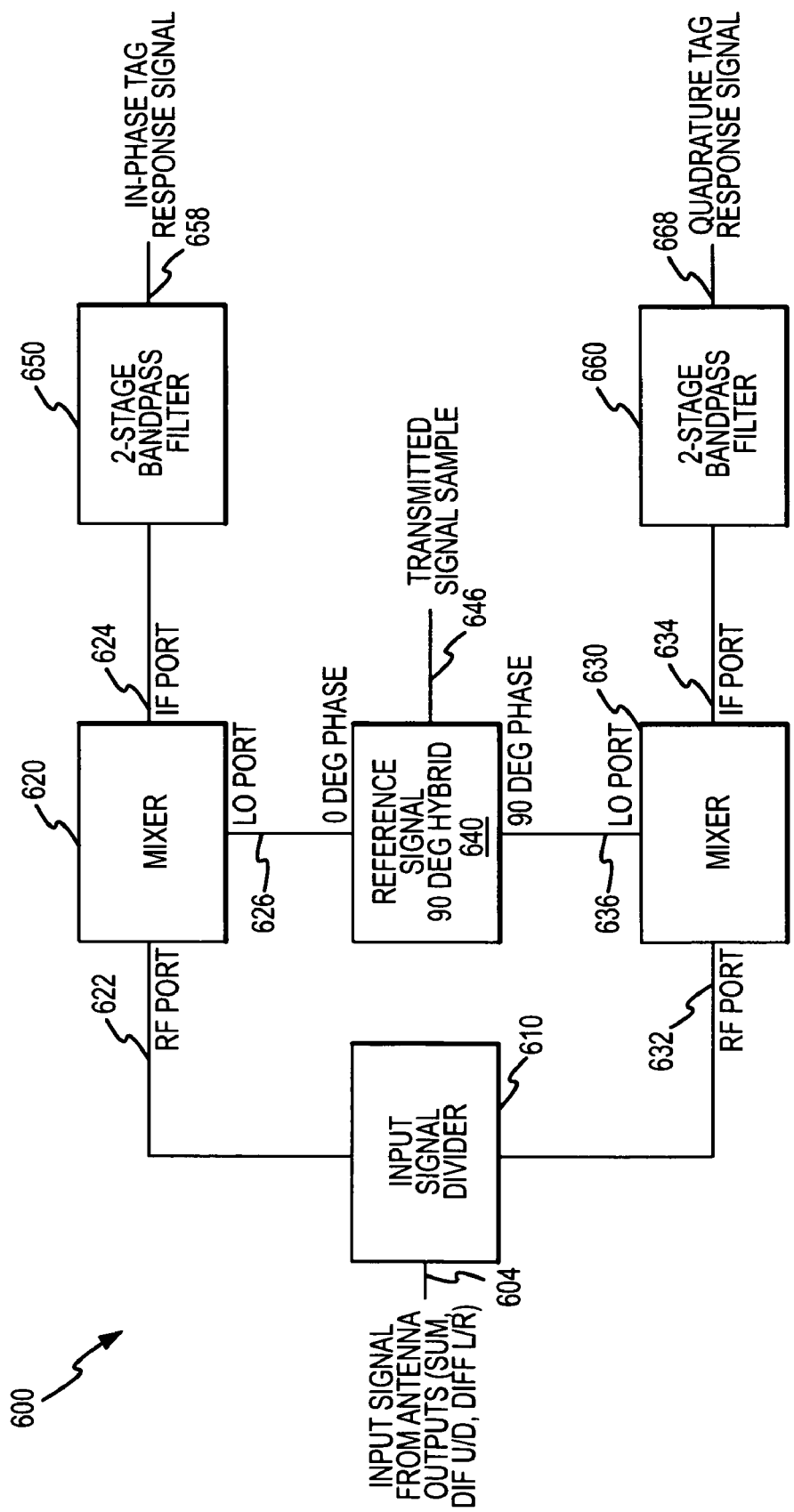
FIG. 6 is a schematic and/or functional block diagram of an embodiment of a receiver processing module provided in a locater of the present invention.

The sum signals 526, 536 from each feed network (U/D and L/R pairs) are combined and processed through a receiver processing module (as shown in FIG. 6). The difference signals 522, 532 (one from each antenna pair) are also routed to a set of receiver modules. The end result for the sum path is to create a single beam at the array face. This single beam at the array face for the locator antenna system allows the locator to read/write an RFID tag on a port much the same as normal antenna would allow a standard RFID tag reader to operate but while enabling the determination of the location of the tag and its corresponding port. For example, in a test system fabricated by the inventor, the sum path was connected to a standard reader with good results.

The difference signals 522, 532 are processed to obtain location information for the port based on signals received from the RFID tag antenna. The array is mechanically modified in some embodiments to provide a physical way of accommodating an inflate/deflate syringe or needle so as to keep the needle substantially perpendicular to the antenna array face, which aligns the needle with the delta pattern (U/D pair and L/R pair) nulls. For example, the array may be arranged as shown in the system 400 of FIG. 4.

Locator devices typically include a receiver processing module (such as module 238 of the RF transmitter/receiver 230 of FIG. 2). As shown in FIG. 6, a receiver processing module 600 is provided for receiving the sum and difference signals from the antenna system. The receiver processing module 600 functions to complete the analog processing for all three antenna system outputs 604 that are fast fed to an input signal divider that outputs to RF ports 622, 632 of a pair of mixers 620, 630. The mixers 620, 630 mix the received high frequency signal with the transmitted signal provided on an LO port 626, 636 from a reference component 640 that utilizes a transmitted signal sample 646 to generate the reference transmitted signal to the mixers 620, 630. By mixing the received signal from the port tag with the transmitted signal, the processing module 600 translates any high frequency tag response signals down to DC.

Filters 650, 660 are provided on the IF ports 624, 634 to follow the signal conversion to separate the port tag's response further from the transmitted signal and, also, from background reflections and to output an in-phase tag response signal at 658 and a quadrature tag response signal 668. In this regard, the filters 650, 660 may be 2-stage bandpass filters. This is possible due to the manner in which the tag imparts information onto the signal that is transmitted to it. Namely, the tag creates a periodic interference at its data rage (e.g., at approximately 32 kHz in some embodiments). It is this frequency-separated tag signal that is used by the reader (or other components of the locator) to read back information from the tag and, significantly for the present invention, for providing direction and/or location. Since the 2-D antenna array provides two difference signals, i.e., one from each dimension (from the L/R pair of antennae and from the U/D antennae pair), moving the antenna array face until both of these difference signals are minimized provides an accurate indication of the location of the RFID tag and, directly or indirectly depending on the access port configuration, the center of the corresponding port face or surface.

Figure 7:
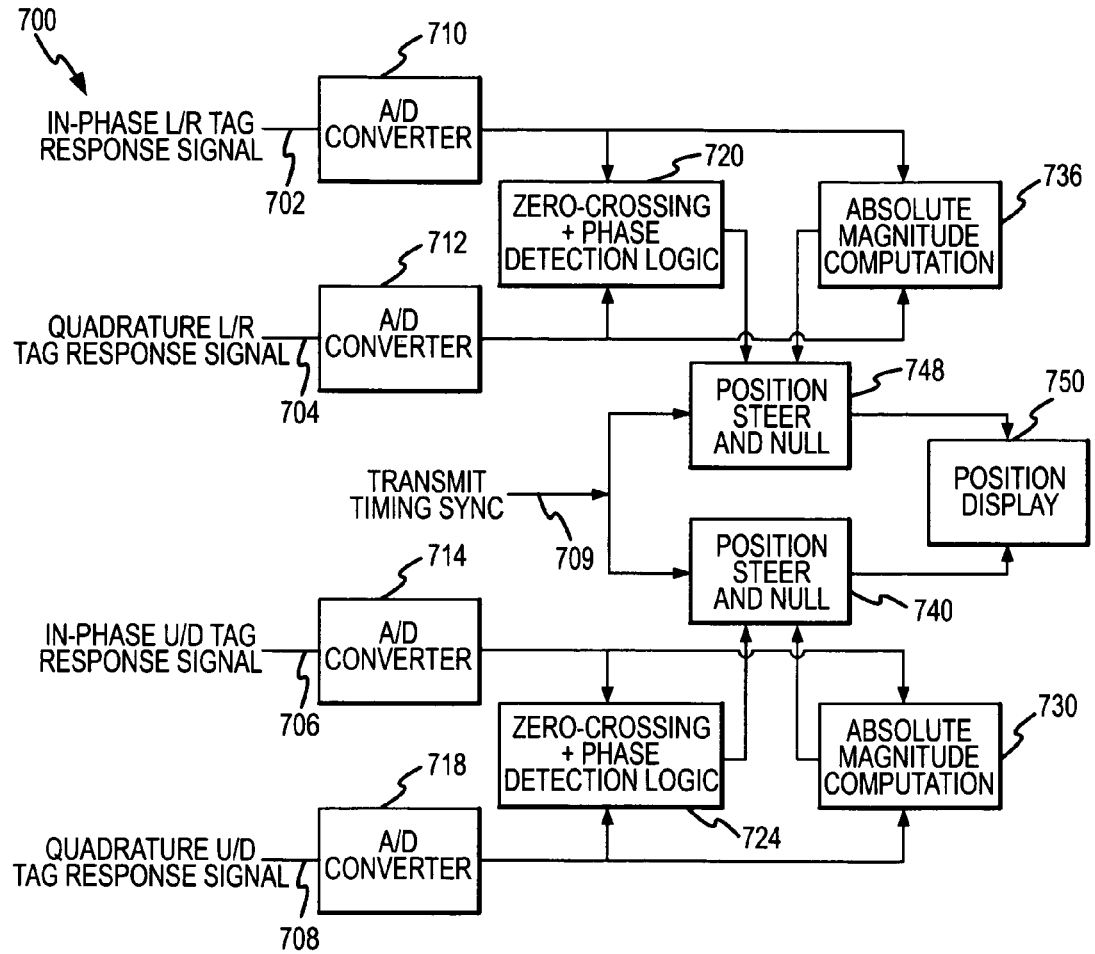
FIG. 7 is a schematic and/or functional block diagram of an embodiment of a location processing module provided in locators of the present invention.

FIG. 7 illustrates a block diagram of a location processing module 700 (such as may be used for module 240 of the locator 210 of FIG. 2). The module 700 takes as input the in-phase tag response signals 702, 706 from the antenna pairs at A/D converters 710, 714. The module 700 also takes as input the quadrature tag response signals 704, 708 from these antenna pairs at A/D converters 712, 718. The module 700 processes these L/R and U/D difference signals 702-708 to provide direction and strength information for determining location information for the port (e.g., for locating the port having the responding RFID tag). To this end, the module 700 also takes as input a transmit timing synchronization signal 709 (e.g., from the RF transmitter/receiver or controller based on a time of transmitting the interrogation signal from the locator to the RFID tag).

Although other software modules/circuitry may be used, the location processing module 700 is shown to process the response signals with zero-crossing and phase detection logic 720, 724 and with absolute magnitude computation logic 730, 736 with the output of these logic elements being provided to the position, steer, and null components 740, 748 with the transmit timing synchronizations signal 709. The computational modules 740, 748 provide their output to position display 750, which may be run as a separate component or as part of the user interface of the locator by the controller/processor to provide on a display location information that can be used by operator to position the locator or, more precisely, the antenna array or system in the locator such that the array face is perpendicular and directly above the center of the port. For example, a visual representation of the location information may be generated by the position display 750 or other components on the display of the locator that provides direction and strength portions of the port location information that should "steer" or direct the operator to move the array face (the locator) directly over and perpendicular to the port (i.e., over the tag). The inflate/deflate needle can then be inserted directly into the center of the port face.

Output from the processing module will be used to direct the user by the user interface on the external control device. An example of the user interface could be a circular array of arrows that light up or change color to direct the user. This user interface could be accomplished with an LCD screen or an array of LED lights. The output will identify a relative distance and direction in which the user needs to move the controller to be over the center of the internal tag and antenna. For example, when the user is 3 to 4 inches southeast of the port center, the controller may register and one light in the northwest quadrant of the circular array may light up indicating the user should move the controller in that direction. In some cases, they are indicated as being relatively far from the target with only one light illuminated. As the user moves the controller in that direction, more lights will illuminate in that quadrant, and then into the next two adjacent quadrants, the northeast and southwest quadrants. As the user gets closer on center to the port, the lights will continue to illuminate until the controller is directly centered. When it is centered, all of the lights will illuminate to confirm the controller is on target. A mark could then be made on the skin to direct the user on where to target the needle, or a guide could be used to direct the syringe and needle towards the port.

Figure 8:
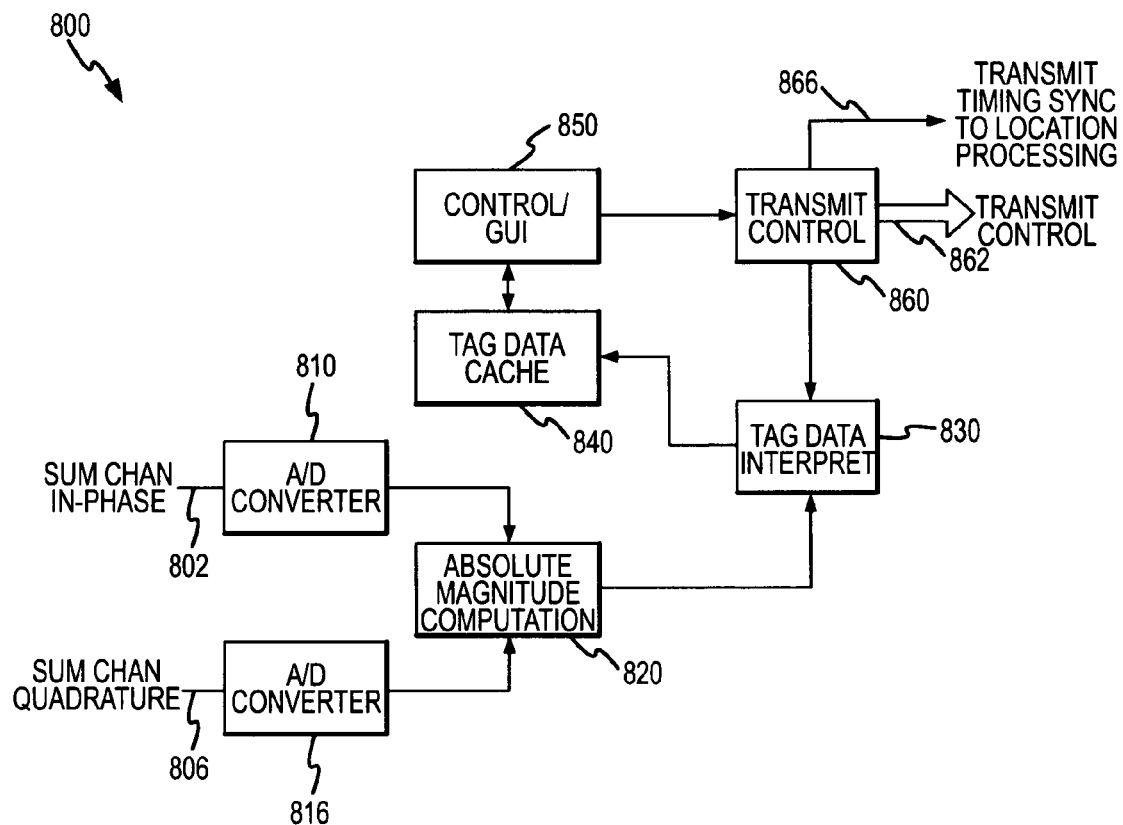
FIG. 8 is a schematic and/or functional block diagram of an embodiment of a tag data interpretation/programming logic module provided in port locators of the present invention.

FIG. 8 illustrates an exemplary tag data processing module 800 (such as may be used for module 250 of locator 210 in FIG. 2). The processing module 800 takes the sum signals 802, 806 from the antenna array or system (e.g., from antenna system 500 of FIG. 5) and converts these signals to digital with converters 810, 816 and performs absolute magnitude computation with element 820. A logic component 830 is provided in module 800 to interpret the tag data, such as port, band, or tag model, type, and/or serial number and/or patient and treatment data. The interpreted/processed data from the tag response signal may be stored in tag data cache 840 and used by the controller and GUI 850 for displaying the data on the locator display (or on another device in wired or wireless communication with the locator). The GUI 850 may also be used to receive and process date input by an operator for writing to the tag memory.

Transmission control element 860 may be used by the locator controller/microprocessor to control transmission of interrogation/read signals and/or write signals (e.g., signals to add or change discretionary information such as a collar/band's previous and most recent inflation amount) 862 to the RFID tag. The transmit control element 860 also provides a transmission timing synchronization signal 866 to the location processing module (such as module 240 or 700). During location processes or after the port is located, the locator (such as locator 200 in FIG. 1) is in some embodiments able to read and write information to the RFID tag of the port such as current device or patient data, inputting physician's or technician's name, the date, and other useful data, with the handheld locator often operating to store or retain the port history/information in its own memory. The display of the locator, which may include visual and audio outputs, typically will display or output the data being read and entered into the port RFID tag as well as providing location information and/or positioning guidance (as discussed above).

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. To practice the invention, the gastric bands that are adjusted by the internal band adjustment systems of the invention may be external to the stomach as shown in FIG. 1, for example, or may be provided or implanted internal to the stomach and/or esophagus, i.e., the gastric bands regulated according to the invention may be intragastric bands. Such an intragastric band may take the same or similar form of the bands described with reference to FIG. 1 or another form (such as forms described in the following incorporated reference), and for example, may be attached and/or implanted in a number of ways such as shown in U.S. Pat. Appl. Publ. No. 2005/0192601, which is incorporated herein by reference.

The invention claimed is:

1. A gastric band system adapted for locating an access port, comprising:
   a gastric band with a fill line having an access port for receiving a needle, wherein the access port comprises a radio frequency identification (RFID) tag; and
   a locator comprising:
      a radio frequency transmitter generating an interrogation signal, wherein the RFID tag operates in response to the transmitted interrogation signal to generate a tag response signal;
      an antenna array with an array face having a minimum of two pairs of antennae positioned an equal distance apart from each other, each of the antennae being spaced an equal distance from a central axis of the antenna array, the array operable by the radio frequency transmitter for transmitting the interrogation signal and receiving the tag response signal; and
      a location processing module processing the tag response signal to determine location information for the access port, wherein the location processing module processes a difference signal for each pair of antennae to determine the location information for the access port, the difference signals being generated based on the tag response signal received by each of the antennae.

2. The system of claim 1, wherein the access port comprises a surface for receiving the needle and the RFID tag comprises an antenna positioned at least partially about the periphery of the receiving surface of the port and wherein the location information is indicative of substantially being in the center of the receiving surface.

3. The system of claim 1, wherein the location information comprises a signal strength value and direction information relative to the array face from the locator.

4. The system of claim 3, wherein the locator further comprises a receiver processing module operating prior to the location processing module to generate an in-phase tag response signal and a quadrature tag response signal from each of the difference signals.

5. The system of claim 1, wherein the locator further comprises a tag data processing module processing a sum signal generated by the antenna array based on the tag response signal to obtain tag data stored in memory associated with the RFID tag.

6. The system of claim 1, wherein the radio frequency transmitter generates a write signal comprising patient treatment data for transmittal to the RFID tag and wherein the RFID tag comprises memory and is operable in response to receiving the write signal to store the patient treatment data in the memory.

7. The system of claim 1, wherein the locator comprises a display operable to display the location information and comprises a receptacle for receiving a syringe with a needle, the receptacle being configured to position the needle perpendicular to the array face and about at the center of the antenna array.

8. A locator apparatus for locating an implantable medical devices such as access ports of gastric bands, comprising:
   a transmitter generating a read signal;
   an antenna array receiving a response signal from an identification tag mounted on an implantable medical device in response to the read signal, wherein the antenna array comprises four antennae mounted on a planar mounting element in a diamond pattern with each of the antennae being a predetermined distance from the center of the diamond pattern and wherein the antenna array generates a difference signal for each opposing pair of the antennae based on the received response signal; and
   a location processing module processing the difference signals to determine location information for the implantable medical device relative to the antenna array.

9. The apparatus of claim 8, wherein the identification tag is an RFID tag and the transmitter is a radio frequency transmitter and the apparatus further comprising a receiver processing module operating to mix the difference signals with a sample of the transmitted read signal and to filter background noise from the mixed signals to generate in-phase tag response signals and quadrature tag response signals and wherein the location processing module processes the in-phase tag response signals and the quadrature tag response signals to determine the location information.

10. The apparatus of claim 9, wherein the determined location information comprises strength information for the response signal and direction information relative to the center of diamond pattern of the antenna array.

11. The apparatus of claim 8, further comprising a housing within which the planar mounting element is mounted, wherein the housing comprises a recessed surface for receiving a syringe, the recessed surface including a needle guide passing through the housing adapted for receiving a needle attached to the syringe, and wherein the needle guide passes through the center of the diamond pattern of the antenna array.

12. The apparatus of claim 8, wherein the antenna array further is configured to output a sum signal for each of the opposing pairs of the antennae and further comprising a tag data processing module processing the sum signals to identify data stored in memory of the identification tag provided in the tag response signal.

13. A system adapted for locating a port, comprising:
   an implantable medical device with a fill line having a port for receiving a needle, wherein the port comprises a radio frequency identification (RFID) tag; and
   a locator comprising:
   a radio frequency transmitter generating an interrogation signal, wherein the RFID tag operates in response to the transmitted interrogation signal to generate a tag response signal;
   an antenna array operable by the radio frequency transmitter for transmitting the interrogation signal and receiving the tag response signal, wherein the antenna array comprises a minimum of two pairs of antennae positioned an equal distance apart from each other, each of the antennae being spaced an equal distance from a central axis of the antenna array; and
   a location processing module processing the tag response signal to determine location information for the access port, wherein the location processing module processes a difference signal for each pair of antennae to determine the location information for the access port, the difference signals being generated based on the tag response signal received by each of the antennae.

14. The system of claim 13, wherein the antenna array the location information comprises a signal strength value and direction information relative to the array face.

15. The system of claim 14, wherein the locator further comprises a receiver processing module operating prior to the location processing module to generate an in-phase tag response signal and a quadrature tag response signal from each of the difference signals.

16. The system of claim 13, wherein the locator further comprises a tag data processing module processing a sum signal generated by the antenna array based on the tag response signal to obtain tag data stored in memory associated with the RFID tag.

17. The system of claim 13, wherein the radio frequency transmitter generates a write signal comprising patient treatment data for transmittal to the RFID tag and wherein the RFID tag comprises memory and is operable in response to receiving the write signal to store the patient treatment data in the memory.

18. An access port for positioning beneath the skin of a patient to provide access to a medical device, comprising:

an antenna for receiving an interrogation signal from a locator;

memory storing port information; and circuitry for responding to the received interrogation signal to generate a response signal comprising at least a portion of the stored port information, whereby the locator functions to determine location information for the access port, wherein the locator comprises an antenna array with an array face having a minimum of two pairs of antennae used to transmit the interrogation signal and receive the response signal, the antennae positioned an equal distance apart from each other, each of the antennae being spaced an equal distance from a central axis of the antenna array, and further wherein the locator comprises a location processing module, wherein the location processing module processes a difference signal for each pair of antennae to determine the location information for the access port, the difference signals being generated based on the response signal received by each of the antennae.

19. The access port of claim 18, wherein the access port further comprises a body with a surface for receiving a needle, wherein the antenna, memory, and circuitry are provided in a radio frequency identification (RFID) tag mounted on or within the body proximate to the needle receiving surface, and the interrogation signal is a radio frequency signal.

20. The access port of claim 18, wherein the access port comprises a surface for receiving a needle and the antenna is positioned at least partially about the periphery of the receiving surface of the port and wherein the location information is indicative of the locator being proximate to the receiving surface of the port.

21. The access port of claim 18, wherein the memory further stores data pertaining to the patient that can be modified by write signals from the locator and wherein the response signal further comprises the stored patient data.

22. The access port of claim 18, wherein the location information comprises a signal strength value and direction information relative to the array face from the locator.

* * * * *

UNITED STATES PATENT AND TRADEMARK OFFICE
CERTIFICATE OF CORRECTION

PATENT NO. : 7,727,143 B2 Page 1 of 1
APPLICATION NO. : 11/444702
DATED : June 1, 2010
INVENTOR(S) : Janel Birk et al.

It is certified that error appears in the above-identified patent and that said Letters Patent is hereby corrected as shown below:

In column 8, line 63, delete "fast" and insert -- first --, therefor.

Signed and Sealed this

Thirteenth Day of July, 2010

David J. Kappos
*Director of the United States Patent and Trademark Office*